(12) United States Patent
Malamud

(10) Patent No.: US 6,760,399 B2
(45) Date of Patent: Jul. 6, 2004

(54) CT SCANNER FOR TIME-COHERENT LARGE COVERAGE

(75) Inventor: Gabriel Malamud, Benyamina (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/117,316

(22) Filed: Apr. 5, 2002

(65) Prior Publication Data

US 2003/0108146 A1 Jun. 12, 2003

Related U.S. Application Data

(63) Continuation of application No. PCT/IL00/00610, filed on Sep. 28, 2000.

(51) Int. Cl.⁷ .................................................. H05G 1/60
(52) U.S. Cl. ................................................ 378/9; 378/4
(58) Field of Search ........................................ 378/9, 4

(56) References Cited

U.S. PATENT DOCUMENTS

| 4,196,352 | A | * | 4/1980 | Berninger et al. | ............. | 378/7 |
|---|---|---|---|---|---|---|
| 4,630,202 | A | | 12/1986 | Mori | | |
| 4,637,040 | A | | 1/1987 | Shoval et al. | | |
| 4,991,190 | A | | 2/1991 | Mori | | |
| 5,228,069 | A | | 7/1993 | Arenson et al. | | |
| 5,485,493 | A | | 1/1996 | Heuscher et al. | | |
| 5,604,778 | A | | 2/1997 | Polacin et al. | | |
| 5,625,661 | A | | 4/1997 | Oikawa | | |
| 5,901,196 | A | | 5/1999 | Sauer et al. | | |
| 5,966,422 | A | * | 10/1999 | Dafni et al. | ................... | 378/9 |
| 6,009,142 | A | | 12/1999 | Sauer et al. | | |
| 6,118,839 | A | | 9/2000 | Dafni et al. | | |
| 6,229,870 | B1 | * | 5/2001 | Morgan | ........................ | 378/9 |

FOREIGN PATENT DOCUMENTS

FR  2 679 435  1/1993

* cited by examiner

Primary Examiner—Craig E. Church
(74) Attorney, Agent, or Firm—Fay, Sharpe, Fagan, Minnich & McKee, LLP

(57) ABSTRACT

In a rotate rotate CT scanner a plurality of source-detector units are mounted on a gantry displaced from each other in the Z direction and the detector units are arranged to acquire data from large volumes of a subject in a single rotation so that the scanner can provide time-coherent images of large organs.

30 Claims, 5 Drawing Sheets

CT SCANNER FOR TIME-COHERENT LARGE COVERAGE

RELATED APPLICATION

This application is a continuation application of PCT application number PCT/IL00/00610, filed Sep. 28, 2000.

FIELD OF THE INVENTION

This invention is concerned with computerized tomographic (CT) systems, and more particularly with such systems equipped with multiple sources of radiation mounted for rotation around the patient at different locations along the longitudinal axis of the patient or object, and further wherein the X-ray beams from each of the sources encompass multiple rows of detectors.

BACKGROUND OF THE INVENTION

The first CT scanners used sources transmitting X-rays with pencil beams and oppositely disposed single detectors which were moved laterally and then rotationally relative to the object. The CT scanners evolved into using X-ray sources transmitting rotatable fan beams along with an oppositely disposed rotatable detector array. In those first rotate-rotate CT scanners, a single row of detectors was used in the detector array. The fan beam angle was sufficiently large so that the fan beam encompassed the single row of detectors. The length of the detectors along the patient or object axis (the Z axis) defined the maximum slice width that could be covered in a "single-shot" without the scanned object or the scanning frame (hereafter referred to as a "scanning unit") being moved during the scan. In the early '90s, a dual slice machine was introduced in which the oppositely disposed detector array, comprised at least two rows of detectors. This increased the coverage in the Z direction. See, for example, U.S. Pat. No. 5,228,069, the contents of which are incorporated herein by reference and made a part hereof.

Another improvement in the scanners was the use of multiple focal spots in the X-ray source, which substantially increased the resolution of the acquired images. See, for example, U.S. Pat. No. 4,637,040, the contents of which are incorporated herein by reference and made a part hereof. Subsequently, multiple X-ray sources at the same Z location were used with detector arrays capable of detecting X-rays from more than one slice. Thus, the detectors were arrays of multiple rows of detectors, so that in a single revolution data for multiple slices were acquired. See, for example, U.S. Pat. No. 5,966,422, the contents of which are incorporated herein by reference and made a part hereof. A further improvement was the provision of helical scans. See, for example, U.S. patent application Ser. No. 08/556,824 and French Patent 9209141, the contents of each of which are hereby incorporated herein by reference.

BRIEF DESCRIPTION OF THE INVENTION

However, until the present invention, there has been no known CT scanner that combines multiple X-ray sources and associated detector array units wherein the units are displaced relative to each other along the Z axis, and wherein each of the arrangements are capable of acquiring multiple slice data.

Besides other advantages, some embodiments that use multiple source detector array arrangements displaced along the Z axis in combination with detector arrays that comprise multiple rows of detectors or large area detectors can provide one or more of the following: large area coverage, high quality time-coherent CT scans, minimize potential cone-beam artifacts, decreases the technical complexities involved in fast data extraction, which are needed for simultaneous imaging of high-resolution volumes of interest (VOI) in the scanned objects. Such combinations of X-ray sources and detector array combinations can provide high-resolution images of complete, large organs such as, for example, the heart in a time-coherent "single shot" image without the need to move the patient or the scanning frame, in order to scan different regions of the volume of interest. This enables a simultaneous scan, or a true cine scan via either "continuous-dynamic" or "gated" axial scans. In cases where a coverage larger than the basic single shot is needed, either a series of axials, or a contiguous helix scan can be done, still accelerating the speed and improving the quality of a single-source system, with a single detector array, having the same or a smaller coverage.

According to an aspect of some embodiments disclosed herein, there is provided a plurality of radiation sources, each source operating with a detector array to form a scanning unit wherein the scanning units are shifted with respect to each other along the longitudinal axis of the object. Optionally, either the distance between arrays or cooperating baffles are designed so that each of the fan beams covers a different object plane or volume. Object planes or volumes may be contiguous.

In accordance with some embodiments of the present invention, a unique CT scanner system is provided. The system comprises a plurality of X-ray sources mounted around the patient at different Z (axial) locations with detector arrays displaced opposite to each of the sources at the different Z locations. Each of the X-ray beams encompasses multiple rows or large area arrays of detectors to form scanning units, so that a rotation around the scanned object (patient or any other object) may provide simultaneous multi-slice image data. In this manner, the scanning units, i.e., the multiple X-ray sources and oppositely disposed large area detectors or multiple rows of detectors, enable time-coherent coverage of a large volume of an object. Such coverage has never before been accomplished. Thus, time-coherent multiple slice or large volume coverage by the detector arrays can be made in a single rotation of the unique CT scanning units, i.e., the multiple sources combine with individual oppositely disposed unique detector array arrangements capable of being displaced from each other in the Z direction.

There is thus provided, in accordance with an embodiment of the present invention, a CT system is provided; the CT system includes a plurality of X-ray sources mounted on a gantry for rotation about an object, said X-ray sources being located at different axial locations, X-ray detector arrays mounted on said gantry individually associated with and situated opposite to each of said X-ray sources at the different axial locations and each of said detector arrays having multiple rows of detectors in the axial direction, said multiple rows of detectors traversing a plurality of slices of the object at said different axial locations during a single rotation.

In some embodiments of the present invention, said plurality of slices encompass a substantial length of an organ in said object. Also in accordance with the above mentioned aspects, the said plurality of slices may encompass at least the entire length of an organ in said object.

The organ may be, for example a human heart.

In accordance with another aspect of the present invention, the detector arrays comprise multiple rows of individual detectors.

In accordance with some embodiments of the present invention, said detector arrays comprise area detectors. The detectors may be sufficiently large to encompass at least the entire length of an organ in said object, or area detectors that are sufficiently large to encompass a substantial length of an organ in the object.

Optionally, at least one of the said X-ray sources utilizes multiple focal spots.

In some embodiments, said X-ray sources with said associated detector arrays and said object move relative to each other in the Z direction to provide a helical scan. Alternatively, said X-ray sources with said associated detector arrays and said object are moved relative to each other in the Z direction to provide a set of n axial scans where $n \geq 1$.

According to an aspect of some embodiments of the present invention, the plurality of sources are rotationally removed from each other by any angle $\theta$ where $0° \leq \theta \leq 180°$.

In an embodiment of the invention, the X-ray sources emit fan beams of X-ray radiation; and the fan beams of at least two of the X-ray sources traverse overlapping sections of the object in the axial direction. Alternatively, the fan beams of at least two of the sources are contiguous to each other in the axial direction. In yet another alternative arrangement, the fan beams of at least two of the sources that illuminate the object are spatially separated in the axial direction. Alternatively, the X-ray beams are cone beams.

According to some embodiments of the present invention, the X-ray detectors are arranged to provide time-coherent multiple slices of the object. Alternatively, the X-ray detector arrays are arranged to provide time-coherent large area views of the patient.

There is further provided, in accordance with an embodiment of the invention a CT system including: a plurality of X-ray sources mounted on a gantry for rotation about an object, a plurality of X-ray detector arrays mounted on said gantry, each being individually associated with and situated opposite to each of the X-ray sources to form a plurality of source-detector units and a source detector unit positioning system for selectively positioning said units at the same axial position or at different axial positions during a single rotation.

There is further provided, in accordance with an embodiment of the invention an imaging method including: mounting a plurality of X-ray sources on a gantry, rotating said gantry around a patient, locating said X-ray sources at said different Z locations, mounting a plurality of detector arrays on said gantry individually associated with and displaced opposite to each of the X-ray sources at different Z locations and simultaneously detecting X-rays that have traversed a plurality of sections of the patient at said different Z locations during a single rotation with said detector arrays.

In accordance with an embodiment of the present invention, said plurality of sections of the patient encompass a substantial length of a human organ, or said plurality of sections of the patient encompass at least the entire length of a human organ and said human organ is an adult heart.

In accordance with an embodiment of the present invention, the detector arrays comprise multiple rows of detectors, where the detectors are individual detectors. Alternatively, the detector arrays comprise wide-area detectors.

According to an embodiment of the present invention, at least one of said X-ray sources utilizes multiple focal spots.

Optionally, a helical scan is provided by moving said X-ray sources with said associated detector arrays and said patient relative to each other in the axial direction.

Alternatively or additionally, moving the X-ray sources with said associated detector arrays and said object relative to each other in the axial direction to provide a set of n axial scans where $n \geq 1$.

Optionally, the plurality of sources are rotationally removed from each other by any angle $\theta$ where $0° \leq \theta \leq 180°$. Optionally, the X-ray sources emit fan beams of X-ray radiation and the fan beams of at least two of the X-ray sources traverse overlapping sections of the patient in the axial direction. Alternatively, the fan beams of at least two of the X-ray sources are contiguous to each other in the axial direction. According to still another alternative, the fan beams of at least two of the sources are spatially separated in the axial direction. The fan beams may be cone beams.

An embodiment of the invention includes arranging the X-ray detectors arrays to provide time-coherent multiple slices of the patient. Alternatively, the X-ray detector arrays are arranged to provide time-coherent large area views of the patient.

There is further provided, in accordance with an embodiment of the invention, a CT imaging method is provided that includes mounting a plurality of X-ray sources on a gantry, mounting a plurality of detector arrays on said gantry, each of said detector arrays being individually associated with each of said X-ray sources, and being placed opposite to said sources to form a plurality of source-detector units and selectively locating said units at the same axial location for detecting X-rays that have traversed the same section of a patient during the single rotation during a single rotation or locating said units at different axial locations for simultaneously detecting X-rays that have traversed a plurality of sections of the patient at said different axial locations during a single rotation.

BRIEF DESCRIPTION OF THE DRAWINGS

Non-limiting embodiments of the present invention are described below with reference to figures attached hereto. In the figures, identical structures, elements or parts that appear in more than one figure are generally labeled with the same numeral in all figures in which they appear. Dimensions of components and features shown in the figures are chosen for convenience and clarity of presentation, and not necessarily shown to scale. The figures are listed below.

GENERAL DESCRIPTION

Figure 1A:
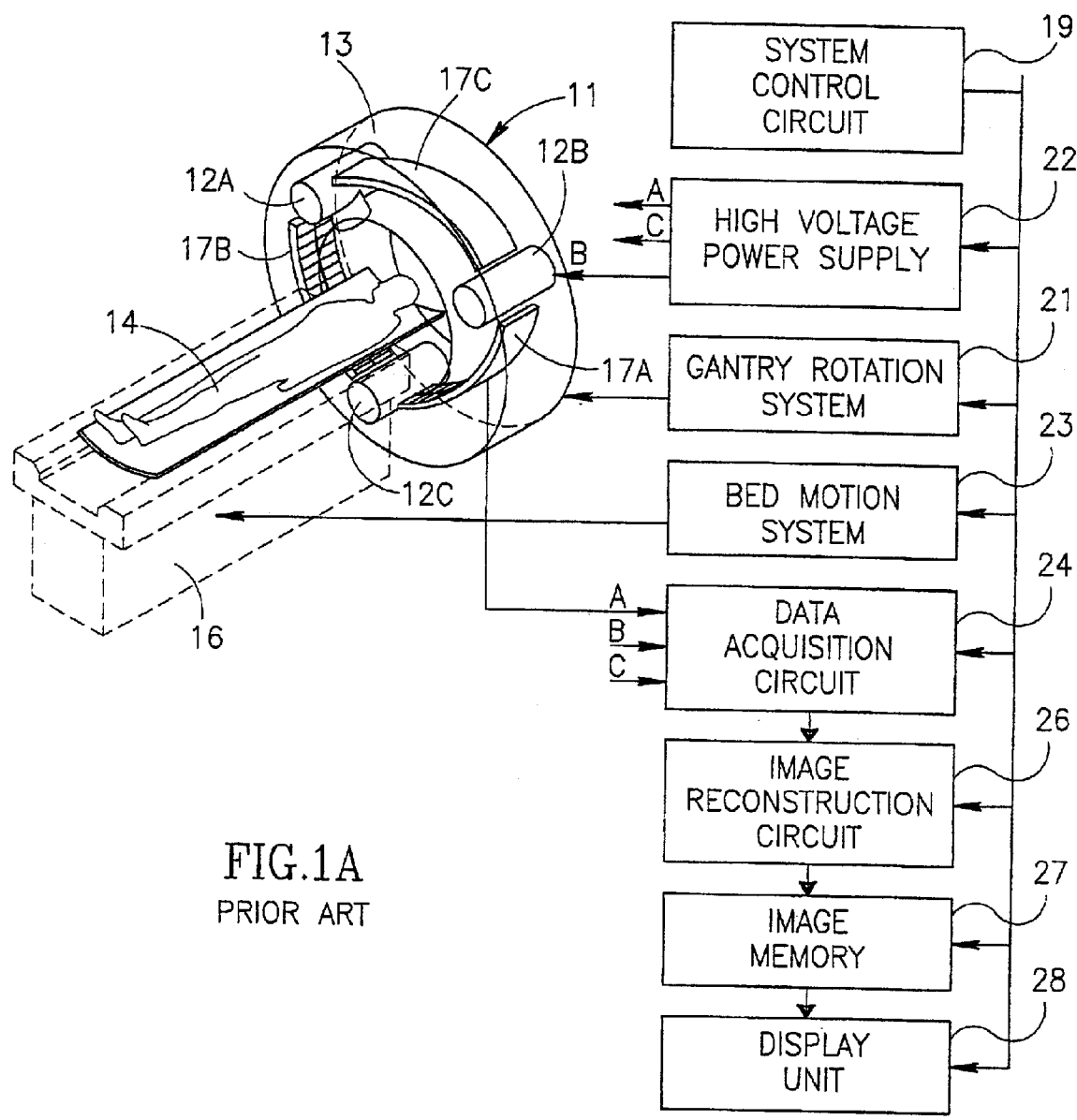
FIG. 1A is a combination pictorial and block diagram showing an example of a prior art CT scanner using multiple sources in conjunction with detector arrays having multiple rows of detectors.

FIG. 1A is a general layout of a third generation (rotate-rotate) scanner 11 comprising three X-ray sources 12A, 12B and 12C, mounted on a gantry 13. A subject or patient 14 to be scanned is shown being supported by means of the bed 16. Fan-shaped X-rays, which traverse a planar section through the subject 14 are detected by a plurality of detector arrays shown by way of example as detector arrays 17A, 17B and 17C.

Figure 1B:
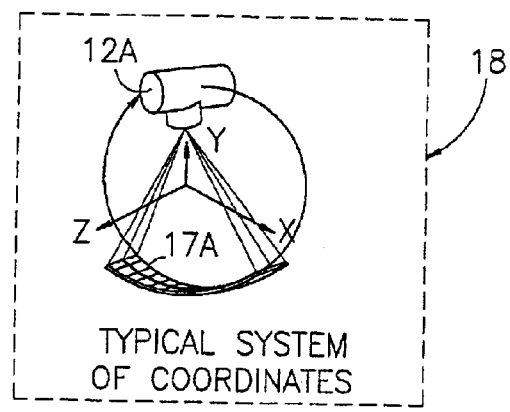
FIG. 1B is a showing of a typical system of coordinates defined by a CT scanning system.

Cartesian coordinate system 18 is shown in FIG. 1B. Therein a common Z axis is defined as being along the longitudinal axis of rotation of the gantry. The Z axis defines a longitudinal axis through the subject. A Y axis is defined as being along a straight line from each of the X-ray sources to the center of revolution of the gantry 13 and the X axes are perpendicular to the above axes. As gantry 13 rotates about the Z axis so do coordinate systems 18 rotate about the Z axis.

According to the prior art showing of FIG. 1A, there are three X-ray sources 12A, 12B and 12C and oppositely disposed detector arrays denoted as 17A, 17B and 17C. However, according to the invention described herein, the number of combined source and detector arrays may be different than three.

Detector arrays 17 detect the X-rays that pass through planar sections in subject 14. The apparatus illustrated in FIG. 1A is referred to as a multiple source, multiple slice CT scanner of the third generation type.

The various operations of the computerized tomography system 11 are controlled by means such as a system control circuit 19. More particularly, circuit 19 controls, among other things, the operation of a gantry rotation system 21. Thus, the prior art gantry 13 with X-ray sources 12A, 12B and 12C revolves about the Z axis, powered and controlled by gantry rotation system 21. The X-ray sources 12A, 12B and 12C are energized by a high-voltage power supply 22, as they rotate around the subject 14. The subject 14 is positioned within a central aperture of gantry 13 by means of a bed motion system 23, which controls the movement of a bed 16.

The maximum coherent coverage of the system is defined by the coverage of each detection array, and by the number of X-ray sources and detection systems. Note that the coverage of the various arrays may differ. Also, at some times and upon clinical needs, only part of the available X-ray sources may be actively irradiating the patient.

The intensity of radiation after its traversal of the patient 14 is detected by detector arrays 17 and acquired by a data acquisition circuit 24. Radiation intensity data from the rays traversing the patient 14 over a range of at least 180° in the gantry revolution plane are used to reconstruct an image by means of image reconstruction circuitry 26, in conjunction with an image memory 27. The reconstructed image is displayed on a display unit 28.

Variations of the system of FIG. 1A are known in the art, and the device of FIG. 1A is useful for illustrative purposes. However, it should be understood that FIG. 1A is not limiting to the invention, which is applicable to a wide variety of CT systems, as known in the art.

In the past, as well as according to the present invention, simultaneously with gantry 13 rotation about the Z axis, subject 14 may be moved by means of bed 16 under the control of bed motion system 23. The bed may also be capable of being moved at oblique angles to the gantry 13 revolution plane i.e., the X,Y plane. Furthermore, in the embodiment of prior art, as well as the present invention, the rotating portions of gantry 13 may revolve continuously for more than one revolution, as is possible with slip-ring construction. The gantries in the prior art, as well as the present gantry, can therefore perform helical scans. However, note that even with helical scans in the prior art, time-coherent, wide-angle coverage of a large organ such as the heart is not possible. In the prior art, each revolution takes a slice that is a smaller portion of the organ. The slices are not acquired at the same time thereby precluding time-coherent coverage of the organ.

Figure 2:
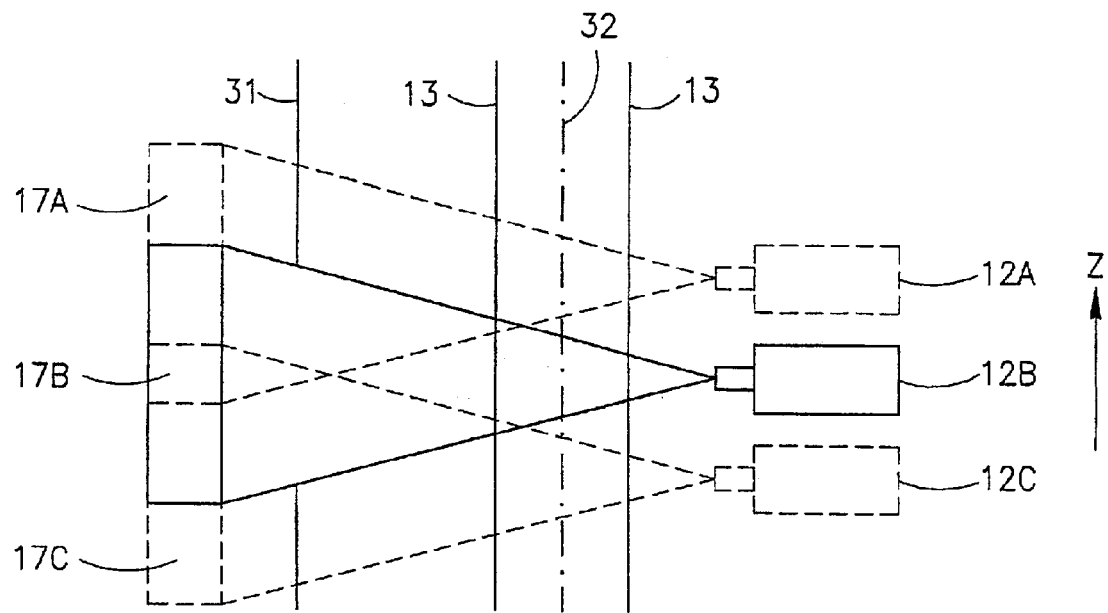
FIG. 2 is a simplified side elevation view illustrating the configuration wherein a plurality of multiple slice images are simultaneously generated according to an embodiment of the present invention.

FIG. 2 shows the three X-ray sources 12A, 12B and 12C displaced along the Z direction, in accordance with an embodiment of the invention. For the sake of simplicity, the sources are shown at the same angular location; although, according to the various embodiments of the present invention the multiple sources may have different angular displacements. The X-ray source 12B is shown with solid lines, while sources 12A and 12C are shown in dotted line form to emphasize that they preferably are actually disposed at different angular positions about the axis of rotation. Note that an optional radial opaque baffle 31 is shown disposed between X-ray sources 12 and X-ray detectors shown indicated generally at 17A, 17B and 17C. The baffle, which is useful when the X-ray source-detector units are at different angles such that the beam angles do not overlap, may rotate in front of each of the detector arrays to block scatter from adjacent slices. The baffle 31 is designed to pass a desired X-ray fan beam. With the X-ray source and detector units at different angular positions a baffle screen may be provided for each source-detector arrangement. Accordingly, in any instant, each of the detectors is in the fan beam of only its associated X-ray source. When the units are at the same angular position, they are spaced apart in the longitudinal direction to assure that the X-ray beams do not overlap.

Any wobble that occurs in the multiple contiguous slice configurations is correctable by providing X-ray detectors which are active along a sufficiently long axial dimension. Then, when the X-ray fan beam sources are operated even under conditions of wobble in the planar mode, all of the wobbly X-ray fan beams still impinge upon an active element of the detector array. In FIG. 2 the axis of rotation is shown at dot dash line 32, while the solid lines 13 are the contours of the patient and/or the X-ray tunnel.

The arrangement using multiple X-ray sources displaced along the Z axis and associated multiple detector or wide-area detector arrays enables large, high-resolution, time-coherent coverage of the scanned object, either free of or with minimal cone beam artifacts even without helix operation. With helix operation, the disclosed arrangement will enable faster helix coverage of objects with large volumes with actual real time coherence. The system is based on using, in the same rotating frame of reference, a group of n(>1) X-ray sources and associated detection array units that are displaced along the Z axis with a distance between them sufficient to minimize cone beam artifacts. The coverage and displacement of these scanning units is calculated so that a contiguous combined coverage is preferably achieved while each of these units is free of cone beam artifacts. The coverage of each of the scanning units is designed so that the angular Z coverage is within an acceptable cone beam level. That is, with minimum cone beam artifacts.

Note that cone beam artifacts are function of both actual cone aperture and of the cone beam correction level via proper reconstruction algorithms. Therefore, the "free-of-cone beams artifacts" coverage definition is a "free" parameter which depend(s) on the specific algorithm and the specific clinical needs.

Figure 3:
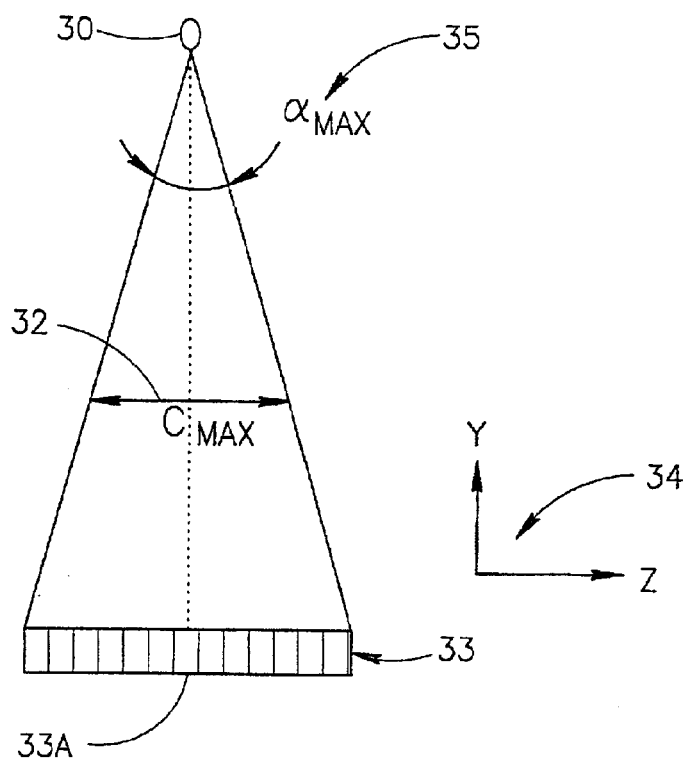
FIG. 3 is an illustration showing the maximum coverage for which cone beam artifacts can be neglected or are tolerable.

FIG. 3 is an illustration of a scanning unit 35 comprising a single source 30, and a detector array 33, in accordance with an embodiment of the invention. In FIG. 3 Cmax is the maximum coverage in the object plane for which cone beam artifacts as a function of the overall system geometry are tolerable. An angle αmax is a corresponding angular coverage in the Y Z plane. The number of detectors in the Z direction and hence the number of slices per scan is shown in FIG. 3 as thirteen. Such a showing is arbitrary and only by way of example. Thus, a different number of detectors can be used within the scope of the present invention. In FIG. 3 the object plane is at 32. The number 34 indicates that FIG. 3 is in the Y Z plane, Z being along the axis of rotation, and Y being the direction between source 31 and detectors 32. Detector array 33, as mentioned before, is shown as having thirteen individual detectors, such as detector 33A. The thirteen individual detectors are used to define individual slices during the scanning and acquisition process.

Figure 4:
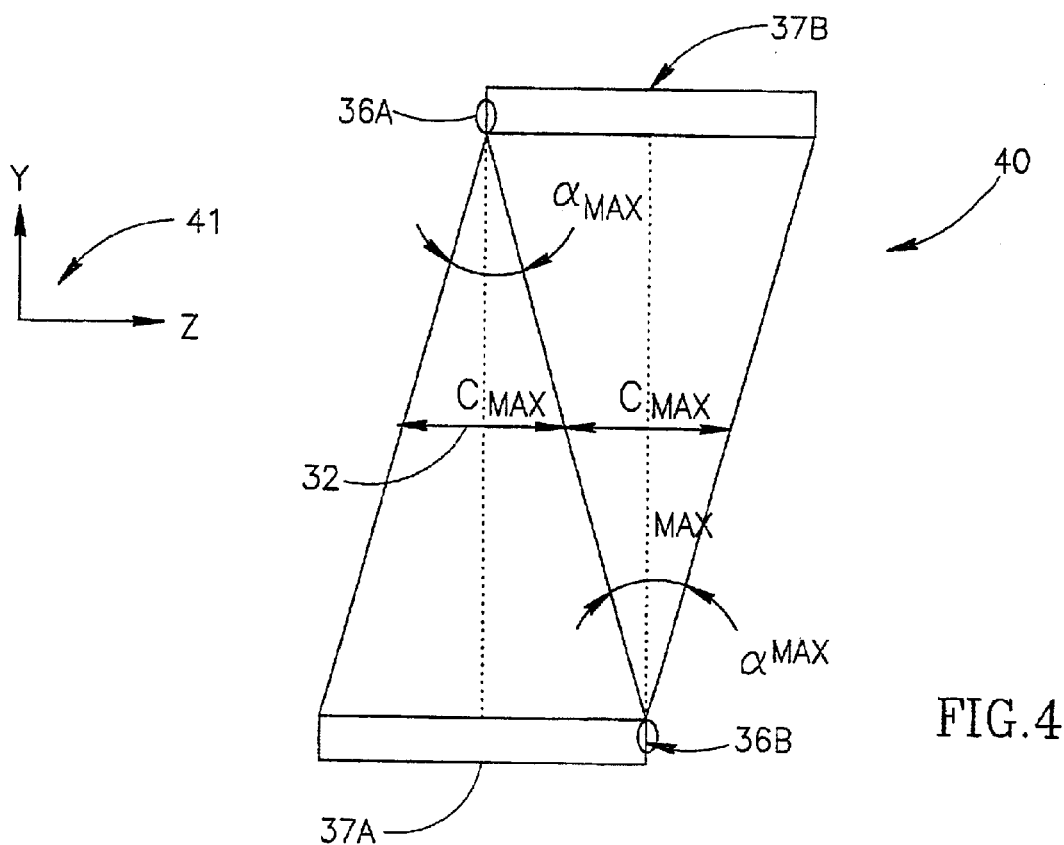
FIG. 4 shows a two source, two array detection system according to an embodiment of the present invention wherein the two sources are shown as being 180° apart on the rotation frame and displaced from each other in the Z direction.

FIG. 4 shows a group 40 of two scanning units, in accordance with an embodiment of the invention, wherein the individual scanning units are displaced from each other along the Z axis. In addition, in FIG. 4 the individual scanning units have an angular displacement between the radiation sources of 180°. It should be recognized that, within the scope of the invention, the angular displacement of individual scanning units can be different from 180°. In FIG. 4 there is shown a source 36A working in conjunction with a detector array 37A. As shown in FIG. 4, at an angle of 180° from source 36A is a source 36B, which operates in conjunction with a detector array 37B. Here again, the source detector combinations are shown by way of example as being in the Y Z plane, indicated at 41. The object plane is shown as C max. Thus, the coverage during rotation of the system is 2C max. The angle α max defines the width of the X-ray fan beam that may be used without creating intolerable cone beam artifacts.

While any angular displacement of the sources from one another can be used, if the angular displacement is smaller than the fan beam in the X Y plane, and if the Z displacement is smaller than array width, the two beams, while irradiating the object simultaneously from the two sources will be partially overlapping on the detector planes, which will prevent proper separated read-out of the signal. In practical terms, then, the displacement of the source detector array scanning units from each other, in both the X and Z directions, is generally at least one fan beam angle α.

Figure 5:
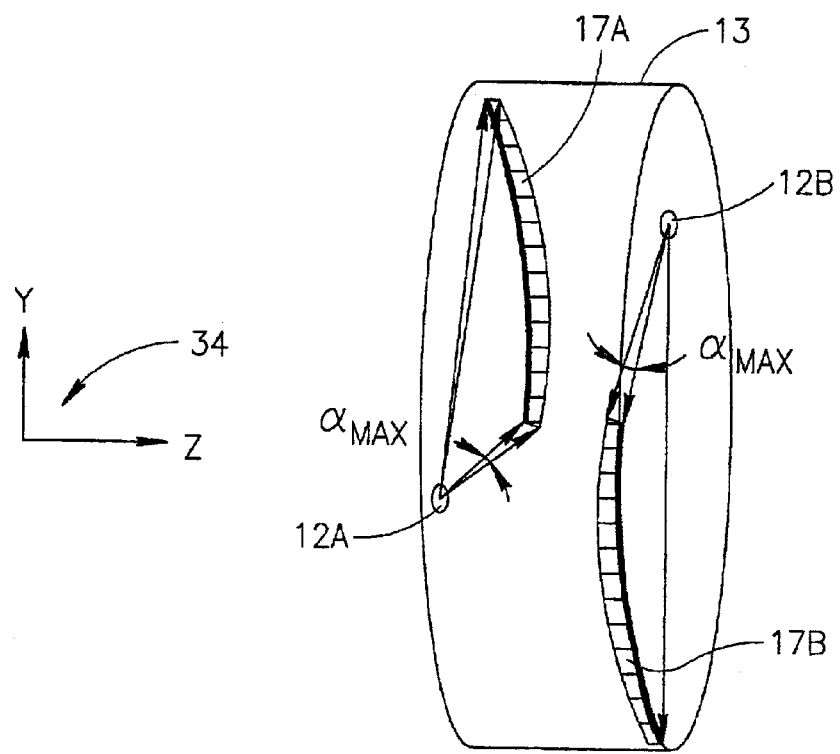
FIG. 5 is a three dimensional illustration of a combined multiple source, multiple detector array scanner wherein the source and combined detectors are rotated to be separated by angles different than 180° and are displaced from each other in the Z direction according to an embodiment of the invention.

FIG. 5 is an exemplary three-dimensional illustration of an inventive multiple source multiple row detector scanner, in accordance with an embodiment of the invention. In this example the sources are separated by an angle different than 180°. More particularly, in FIG. 5 there is shown a source 12A which illuminates a detector array at 17A. A second source 12B illuminates a detector array 17B. In the detector arrays, the rows of detectors extend in the Z direction. The arrays also extend in the rotational direction. The fan beam is shown as extending in the Z direction over an angle α max. The rotational distance between source 12A and 12B is different than 180°. FIG. 5 illustrates and emphasizes that it is not required that the sources be separated from each other by 180°, or even be separated by equal divisions of 360°. Thus, it is not necessary when there are two source detector array units that they be separated by 180°, or when there are three source detector array units that they be separated by 120°.

Figure 6:
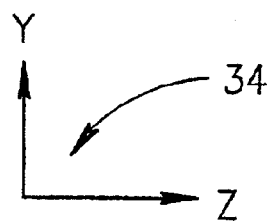
FIG. 6 is a schematic illustration of a group of a four focal spot source and detector units where Z displacement between the combined adjacent source and detector units is defined by $\Delta Z=Cmax$ and the angular displacement is shown as 180°; according to an embodiment of the invention.
Figure 6:
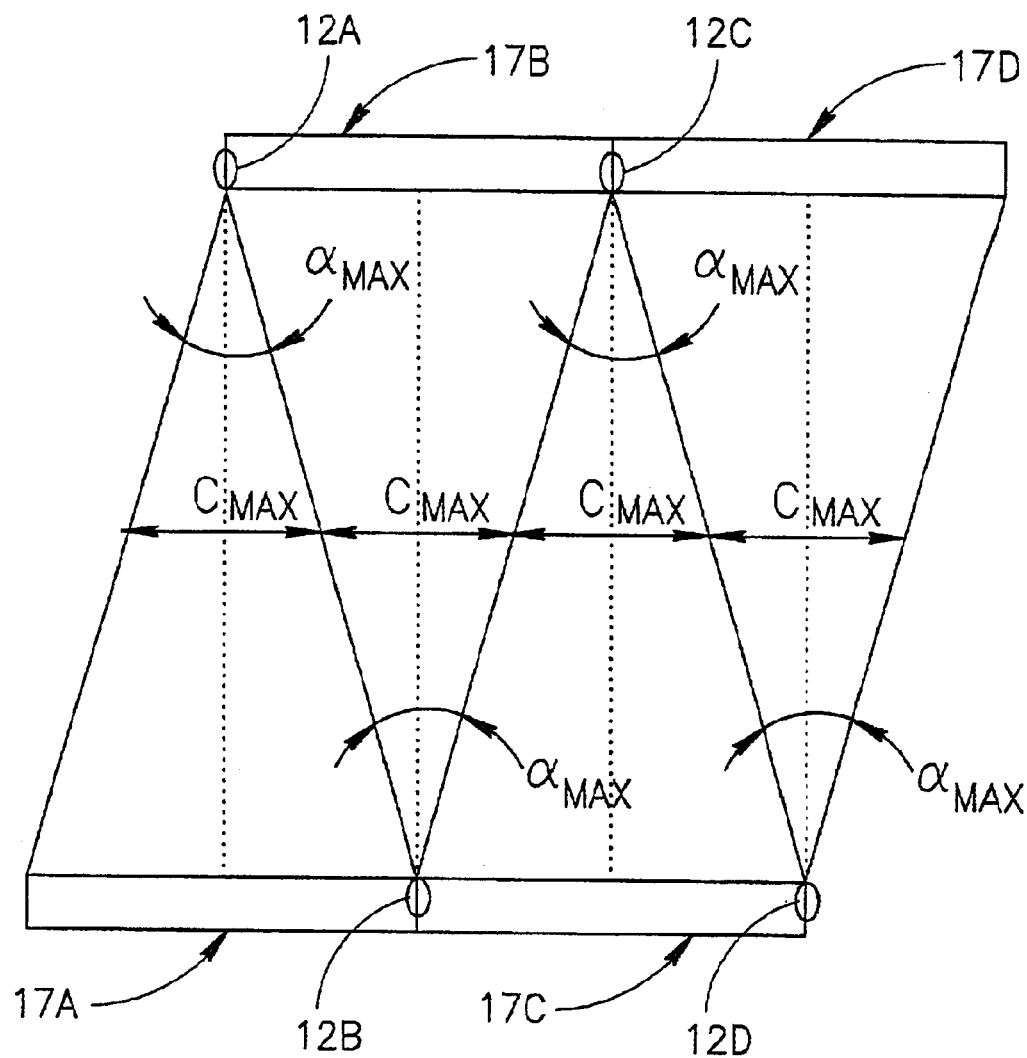

FIG. 6 is a showing of a group of four X-ray source detector array units. The angular displacement therein between adjacent CT scanning units is shown as being 180°. The ΔZ displacement is defined by the conical fan beam α which illuminates the object plane. The Z coverage of the four CT scanning units is 4C max at the object plane. The Z spacing between the CT scanning units is not restricted to the C max distance, but is rather a subject for optimization. Within the scope of the invention, coverage of an "object plane" may use a somewhat smaller displacement that provides less than contiguous coverage, or may use a bigger displacement to obtain contiguous coverage, or may use a still bigger displacement to obtain simultaneous coverage. The coverage in an embodiment of the invention is ideally equal to or a substantial part of the longitudinal length of an adult heart i.e., 10–15 cm.

In FIG. 6, four CT scanning units are shown. They are comprised of sources 12A, 12B, 12C and 12D. Each source is individually associated with oppositely disposed detector arrays such as detector array 17A, 17B, 17C and 17D, respectively. It should be noted that the sources could be dual focus spot X-ray sources. With the embodiment shown in FIG. 6, twice as much coverage may be obtained as in the embodiment of FIG. 4. Here again, the Y and Z axes are shown at 34.

Figure 7:
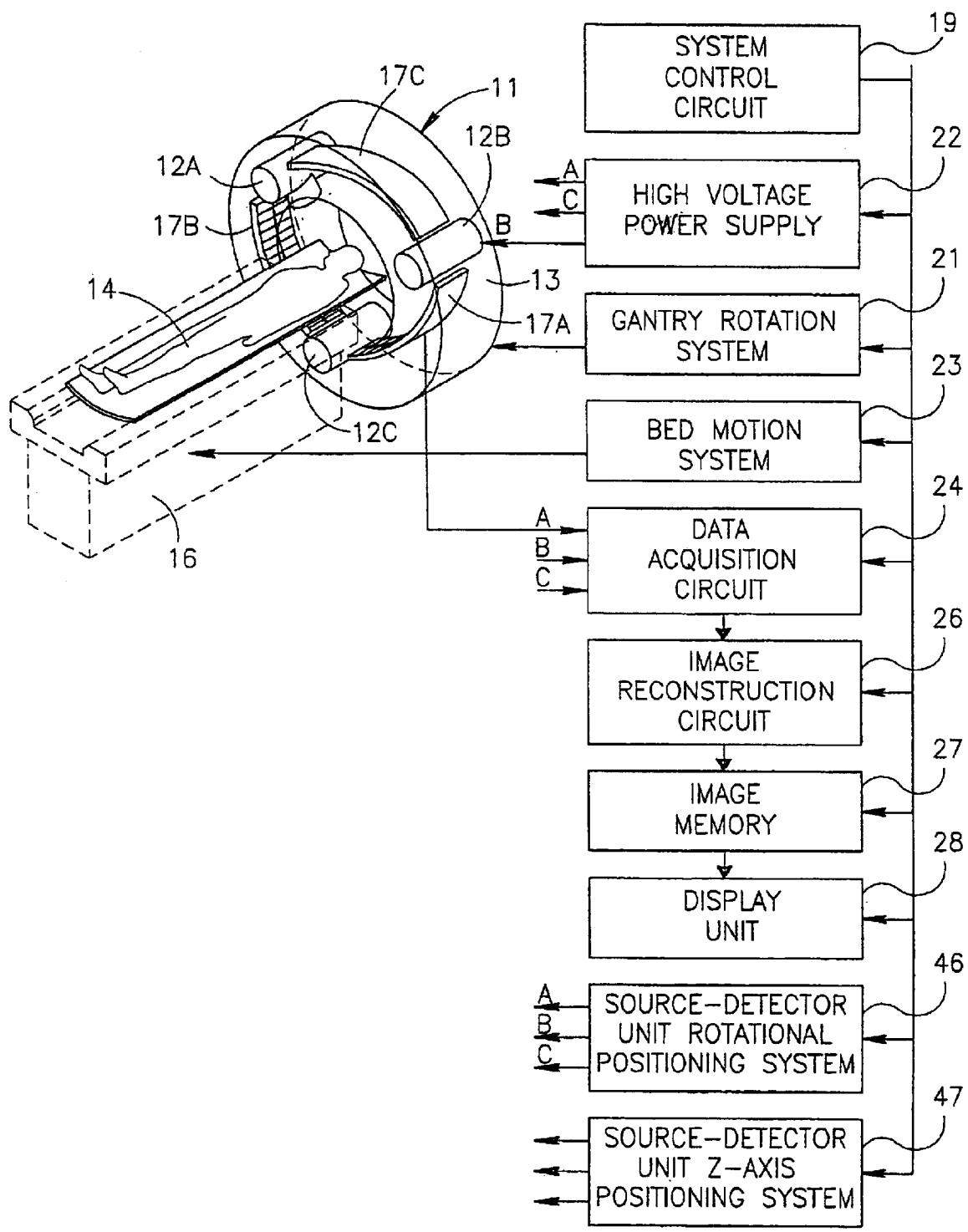
FIG. 7 is a combination pictorial and block diagram showing of a CT scanner according to an embodiment of the invention including CT scanning units, each comprising an X-ray source operating with an oppositely disposed detector array, each unit capable of being positioned separately at different rotational and/or longitudinal locations along the Z axis.

FIG. 7 is a block diagram illustration of an embodiment of the invention showing some features not in the prior art. In FIG. 7 three CT scanning units are shown. They are shown positioned with all of the CT scanning units in the same Z locations i.e., in the same plane; which is one option. However, according to FIG. 7, there is also included a rotational positioning system 46 for individually varying the angular displacement rotation of each of the CT scanning units, comprising sources 12 and oppositely disposed individually associated detector arrays 17. The rotational positioning system is operational when the units are at different longitudinal positions. Block 47 shows a system for individually positioning each of the source detector units along the Z axis, either in the same plane or in different frames or in combinations thereof.

Thus, according to the system disclosed in FIG. 7, all of the individual CT scanning units can be positioned at the same Z axis location to operate as in the prior art, or they can each individually be positioned along the Z axis, at a different Z axis location, in accordance with the system explained with regard to FIG. 4, for example. Thus, the disclosed system provides versatile scanning arrangements including prior art features and new features.

The Z displacement of the CT scanning units can be fixed or variable. Also, the rotational displacement of the combined source-detector units can be fixed or variable. Thus, within the scope of the invention, as shown in FIG. 7, the scanning apparatus incorporates a capability to change the Z position of each combined source detector unit; that is, each source-detector unit can be independently moved in the Z direction. The system of FIG. 7 selectively combines the advantages of gantries having multiple sources and detectors in a single plane and multiple sources and detector units, each in a different plane. When the source detector units are in different planes, it is advisable to use all source detector units in the different planes simultaneously. However, certain time lags between scan frames may be introduced in order to achieve certain time dependencies or to stay within power supply limits, or in order to reduce the scatter radiation which crosses between detection frames.

The systems presented enable the acquisition of relatively large coverage, time-coherent images without the need for helical motion. However, the scanners described herein, of course, can be utilized in the helical mode while providing the large coverage for very high-scan speeds. It is in such cases that the variable Z spacing between the different source detection frames is a useful adaptation, since it allows for matching the spacing to the helix angle. It is also possible in the system for certain scans to use only some of the source detection systems, while others are not used. Similarly, the X-ray sources can be energized simultaneously or during separated time slots in order to effectively provide multi-energy modalities.

A person skilled in the art of X-ray detection will appreciate that the present invention is not limited to a particular detector array or to particular X-ray sources, but rather to any apparatus that deals with the intensity and position of the X-rays. In particular, detector arrays, such as detector arrays 17A–17D may comprise multiple-detector elements, multiple-segmented detector elements in an array of single detectors or continuous wide-area media responsive to X-rays that also provides position read-outs.

As used herein, the terms "comprise", "include" or "have" or their conjugates mean "including but not necessarily limited to."

Although the invention has been described with reference with particular embodiments, the invention is not confined to the specific embodiments described herein and above, but rather to the general scope of the claims attached hereto.

What is claimed is:

1. A CT system including:
   a plurality of cone beam x-ray sources mounted on a gantry for rotation about an axis of rotation, said x-ray sources: (1) generating a cone beam of radiation for volumetric imaging, (2) being angularly offset at different angular locations around the axis of rotation, and (3) being axially offset at different axial locations along the axis of rotation;
   a plurality of two-dimensional, multi-slice x-ray detector arrays mounted on said gantry for rotation about the axis of rotation, each detector array situated opposite to an associated one of said cone-beam x-ray sources, the detector arrays being axially offset at the different axial locations along the axis of rotation, each of said detector arrays having multiple rows of detectors in the axial direction, said multiple rows of detectors defining a plurality of slices at said different axial locations along the axis of rotation during a single rotation;
   the detector arrays and the x-ray sources being axially offset such that the slices defined by each of the detector arrays overlap only in part with the slices defined by an adjacent one of the detector arrays.

2. The CT system of claim 1 wherein said plurality of sources are rotationally removed from each other by any angle θ, where θ=120°.

3. The CT system of claim 1 wherein the plurality of slices defined cumulatively by the plurality of detectors encompass an elongated region that is longer along the axis than any one of the detector arrays.

4. The CT system of claim 3 wherein the elongated region is shorter than a sum of axial lengths of all of the detector arrays.

5. The CT system of claim 1 wherein said detector arrays comprise multiple rows of individual detectors.

6. The CT system of claim 1 wherein said detector arrays comprise area detectors.

7. The CT system of claim 1 wherein said x-ray sources with associated detector arrays and an object to be scanned are moved in increments relative to each other in the axial direction to provide a set of n axial scans, where n≧1.

8. The CT system of claim 1 wherein said x-ray sources with said associated detector arrays and an object to be scanned move relative to each other in the axial direction to provide a helical scan.

9. The CT system of claim 1 wherein at least one of the said x-ray sources utilizes multiple focal spots.

10. The CT system including:
    a plurality of x-ray sources mounted on a rotating gantry which rotates around an axis of rotation, the x-ray sources being axially offset from each other and angularly offset from each other angularly around the axis of rotation, each radiation source generating an x-ray beam that spans a plurality of slices;
    a plurality of multi-slice detector arrays mounted on said rotating gantry, each of the detector arrays extending a plurality of slices axially;
    each of the multi-slice detector arrays being mounted opposite to and being individually associated with one of said plurality of x-ray sources,
    such that said multi-slice detector arrays provide time-coherent data from each of a plurality of axially offset volumetric regions to facilitate generating time-coherent volumetric images of the axially offset volumetric regions.

11. The CT system of claim 10 wherein said x-ray sources and the detector arrays are mounted on the rotating gantry such that:
    the slices of at least two of the volumetric regions overlap in the axial direction.

12. The CT system of claim 10 wherein said x-ray sources and the detector arrays are mounted to the rotating gantry such that;
    at least one of the volumetric regions is spatially separated in the axial direction from the other volumetric regions to facilitate generating time-coherent images of axially displaced volumetric regions.

13. The CT system of claim 10 where the x-ray sources and the multi-slice detector arrays are mounted to the rotating gantry such that time-coherent views spanning an axially elongated volume of an examined patient are generated.

14. The CT system including:
    a plurality of cone beam x-ray sources mounted on a gantry for rotation about an object;
    a plurality of multi-slice x-ray detector arrays mounted on said gantry, each being individually associated with and situated opposite to a corresponding one of the cone-beam x-ray sources to form a plurality of multi-slice source detector units; and
    a multi-slice source detector unit positioning system for selectively positioning said multi-slice source units at the same axial position or at different axial positions.

15. A CT scanning method including:
mounting a plurality of multi-slice x-ray sources on a gantry;
rotating said gantry around a patient;
locating said x-ray source at different longitudinal locations;
mounting a plurality of multi-slice detector arrays on said gantry individually associated with an displaced opposite to each of the x-ray sources at different longitudinal locations; and
simultaneously detecting x-rays that have traversed a plurality of multi-slice sections of the patient at said different longitudinal locations during a single rotation with said multi-slice detector arrays.

16. The CT scanning method of claim 15 wherein said plurality of multi-slice sections of the patient encompass at least the entire length of a human organ.

17. The CT scanning method of claim 15 wherein said detector arrays comprise multiple rows of detectors.

18. The CT scanning method of claim 15 wherein said detector arrays comprise multiple rows of individual detectors.

19. The CT scanning method of claim 15 wherein said detector arrays comprise wide-area detectors.

20. The CT scanning method of claim 15 wherein at least one of said x-ray sources utilizes multiple focal spots.

21. The CT scanning method of claim 15 further including:
moving said x-ray sources with said associated detector arrays and said patient relative to each other in a longitudinal direction as the gantry rotates to provide a helical scan.

22. The CT scanning method of claim 15 including moving said x-ray sources with said associated detector arrays and said patient relative to each other in the axial direction to provide a set of n axial scans, where $n \leq 1$.

23. The CT scanning method of claim 15 wherein said plurality of multi-slice sections of the patient encompass a substantial length of a human organ.

24. The CT scanning method of claim 23 wherein said human organ is an adult heart.

25. The CT scanning method of claim 15 wherein the x-ray detector arrays are arranged to provide time-coherent large area views of the patient.

26. The CT scanning method of claim 15 wherein said plurality of source are rotationally removed from each other by any angle $\theta$ where $0° \leq \theta \leq 180°$.

27. The CT scanning method of claim 15 wherein:
said x-ray sources emit cone beamss of x-ray radiation; and
the cone beams of at least two of the x-ray sources traverse overlapping adjacent multi-slice sections of the patient in a longitudinal direction.

28. The CT scanning method of claim 15 wherein:
said x-ray sources emit cone beams of x-ray radiation; and
the cone beams of at least two of the x-ray sources are contiguous to each other in a longitudinal direction.

29. The CT scanning method of claim 15 wherein:
said x-ray sources emit cone beams of x-ray radiation; and
the cone beams of at least two of the sources are spatially separated into an axial direction such that at least two of the multi-slice regions are physically separated.

30. A CT imaging method including:
mounting a plurality of cone-beam x-ray sources on a gantry;
mounting a plurality of two-dimensional detector arrays on said gantry; each of said detector arrays being individually associated with each of said x-ray sources, and being displaced opposite to said sources to form a plurality of volume scanning source detector units; and
selectively locating said units at different axial locations for simultaneously detecting x-rays that have traversed a plurality of volumetric sections of the patient at said different axial locations during a single rotation, at least two of the volumetric sections partially overlapping.

* * * * *